(12) United States Patent
Yodfat et al.

(10) Patent No.: US 9,724,468 B2
(45) Date of Patent: *Aug. 8, 2017

(54) DEVICES AND METHODS FOR ADJUSTING BASAL DELIVERY PROFILE

(71) Applicant: Roche Diabetes Care, Inc., Indianapolis, IN (US)

(72) Inventors: Ofer Yodfat, Maccabim-Reut (IL); Gali Shapira, Haifa (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/979,693

(22) Filed: Dec. 28, 2015

(65) Prior Publication Data

US 2016/0106917 A1    Apr. 21, 2016

Related U.S. Application Data

(63) Continuation of application No. 13/376,040, filed as application No. PCT/IL2010/000437 on Jun. 3, 2010, now Pat. No. 9,248,231.

(Continued)

(51) Int. Cl.
*A61M 5/172* (2006.01)
*A61M 5/14* (2006.01)
*A61M 5/142* (2006.01)

(52) U.S. Cl.
CPC .......... *A61M 5/172* (2013.01); *A61M 5/1413* (2013.01); *A61M 5/14248* (2013.01);
(Continued)

(58) Field of Classification Search
CPC ............ A61M 5/14248; A61M 5/1413; A61M 5/1723; A61M 2205/3539;
(Continued)

(56) References Cited

U.S. PATENT DOCUMENTS 5,368,562 A * 11/1994 Blomquist ............ A61M 5/172
                                              604/246
9,248,231 B2 * 2/2016 Yodfat ................ A61M 5/1413
(Continued)

FOREIGN PATENT DOCUMENTS

WO    2008078318 A2    7/2008
WO    2008078319 A1    7/2008
(Continued)

OTHER PUBLICATIONS

DCCT Trial, N. Engl J. Med 1993; 329: 977-986.
(Continued)

*Primary Examiner* — Manuel Mendez
(74) *Attorney, Agent, or Firm* — Dinsmore & Shohl LLP

(57) ABSTRACT

The present disclosure presents systems, devices and methods for administration of a therapeutic fluid to the body of a patient at a transient basal delivery profile, and enabling modification of the transient profile. Some embodiments include a user interface enabling input of one or more transient basal related parameters, and a processor having a basal programming application operating thereon. The basal programming application configured for determining a transient basal profile based on at least one or more transient basal related parameters. The transient basal profile comprises a plurality of phases and wherein each of the plurality of phases is characterized by a duration and at least one basal rate. In some embodiments, at least one of the plurality of phases includes either a basal overshot or a basal undershot. Some embodiments may also include a pump for dispensing the therapeutic fluid from a reservoir to the body of the patient.

24 Claims, 9 Drawing Sheets

Related U.S. Application Data

(60) Provisional application No. 61/183,976, filed on Jun. 4, 2009.

(52) U.S. Cl.
CPC . *A61M 5/1723* (2013.01); *A61M 2005/14208* (2013.01); *A61M 2005/14268* (2013.01); *A61M 2205/3379* (2013.01); *A61M 2205/3569* (2013.01); *A61M 2205/3592* (2013.01); *A61M 2205/52* (2013.01); *A61M 2230/005* (2013.01); *A61M 2230/201* (2013.01); *A61M 2230/63* (2013.01)

(58) Field of Classification Search
CPC ......... A61M 2005/14208; A61M 2005/14268; A61M 2205/3592
USPC ....... 604/503, 65–67, 131, 151; 128/DIG. 1, 128/DIG. 12, DIG. 13
See application file for complete search history.

(56) References Cited

U.S. PATENT DOCUMENTS

| | | | |
|---|---|---|---|
| 2002/0019606 A1* | 2/2002 | Lebel | A61M 5/172 604/66 |
| 2003/0050621 A1* | 3/2003 | Lebel | A61M 5/14276 604/890.1 |
| 2003/0060753 A1 | 3/2003 | Starkweather et al. | |
| 2004/0077997 A1* | 4/2004 | Jasperson | A61M 5/14276 604/67 |
| 2005/0272640 A1 | 12/2005 | Doyle et al. | |
| 2007/0006956 A1 | 1/2007 | Park et al. | |
| 2007/0106218 A1 | 5/2007 | Yodfat et al. | |
| 2007/0112298 A1 | 5/2007 | Mueller et al. | |
| 2007/0191702 A1 | 8/2007 | Yodfat et al. | |
| 2008/0147050 A1* | 6/2008 | Mann | A61M 5/14244 604/890.1 |
| 2008/0214916 A1 | 9/2008 | Yodfat et al. | |
| 2008/0215035 A1 | 9/2008 | Yodfat et al. | |
| 2008/0319384 A1 | 12/2008 | Yodfat et al. | |

FOREIGN PATENT DOCUMENTS

| | | |
|---|---|---|
| WO | 2009016636 A2 | 2/2009 |
| WO | 2009125398 A2 | 10/2009 |

OTHER PUBLICATIONS

UKPDS Trial, Lancet 1998; 352: 837-853.
BMJ 1998; 317 (7160: 703-13.
EDIC Trial, N Engl J Med 2005; 353 (25): 2643-53.
ISR and Written Opinion for International Application No. PCT/IL2010/000437, mailed Nov. 8, 2010.
Extended European Search Report pertaining to Application No. PCT/IL 2010000437.

* cited by examiner

DEVICES AND METHODS FOR ADJUSTING BASAL DELIVERY PROFILE

CROSS-REFERENCE TO RELATED APPLICATIONS

This application is a continuation of U.S. patent application Ser. No. 13/376,040, filed Apr. 11, 2012, which is a 35 U.S.C. §371 national stage entry of PCT/IL2010/000437, filed Jun. 3, 2010, which claims priority to U.S. provisional application No. 61/183,973, filed Jun. 4, 2009, the entire disclosure of which is herein incorporated by reference.

FIELD

Methods and devices for sustained medical infusion of therapeutic fluids (e.g., insulin) are described herein. Some embodiments relate to portable infusion devices and methods for adjusting a profile/pattern of the therapeutic fluid delivery. Some embodiments relate to skin securable insulin dispensing devices and methods employing interim or transient adjustment of basal doses.

BACKGROUND

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin in correspondence with blood glucose levels, maintaining near constant glucose levels in the body.

Much of the burden of the disease to the patients and to health care resources is due to long-term tissue complications, which affect both small blood vessels (microangiopathy, causing eye, kidney and nerve damage) and large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin (HbAlc) [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining euglycemia by frequent glucose measurements and adjustment of insulin delivery accordingly is of utmost importance.

Conventional insulin pumps can deliver rapid acting insulin 24 hours a day through a catheter placed under the skin. The total daily insulin dose can be divided into basal and bolus doses.

Insulin boluses are delivered before or after meals to counteract carbohydrates loads or during episodes of high blood sugar levels.

Basal insulin is delivered continuously over 24 hours, and keeps the blood glucose levels within acceptable ranges between meals and overnight. Diurnal basal rates can be pre-programmed or manually changed according to various daily activities.

Conventional insulin pumps provide an option to change basal delivery profile for a predetermined time period, as described in U.S. Patent Application No. 2007/006956 assigned to MiniMed. The user can change basal rate to a new rate (referred-to as "Temporary Basal Rate" or "TBR") which can be a fixed percentage of the Current Basal Rate (hereinafter "CBR") (i.e., the basal rate remains a percentage of a constant value). For example, if a CBR of 1 U/h at 12 am was followed by a reduction of 50% of the CBR for a period of time of 2 hours, a TBR of 0.5 U/h would result between 12 am and 2 am. After 2 am, the basal rate would typically return to the former CBR before the change, i.e. 1 U/h. It is worth noting, that the term "current" (as used with Current Basal Rate) is meant to mean the present/now (occurring presently) and/or anticipated, planned, prospective and programmed corresponding to future events.

In another example, the TBR may change its absolute value but maintain a fixed percentage of the prospective basal rate, i.e. the basal rate that would have otherwise been delivered. That is, the basal rate remains at a uniform percentage of the basal profile as it varies. For example, if the CBR was supposed to be 1 U/h between 8 am and 12 pm, and 2 U/h between 12 pm and 8 pm, a reduction of 50% of the CBR for a period of 4 hours starting at 10 am, would result in a TBR of 0.5 U/h between 10 am and 12 pm, and 1 U/h between 12 pm and 2 pm. After 2 pm, the basal rate would return to its prospective value, i.e. 2 U/h.

Such temporary changes in basal delivery rates appear to provide a convenient way to adjust insulin delivery in response to a temporary change in a user's daily activity.

Pharmacodynamic observations have shown that the time between basal delivery rate change and metabolic effect is very long (in the order of hours). The conventional basal rate changing methods as described above do not comply with human physiology because they do not consider this delay between basal delivery rate change and metabolic effect. For example, before extreme exercise a patient had reduced basal rate from 1 U/h to 0.5 U/h for 2 hours. In practice, steady state at 0.5 U/h was achieved after 2 hours. Consequently, the patient was overdosed during exercise and under dosed during recovery from exercise. This way, the application of temporary basal insulin delivery is being employed inefficiently and may risk patient's health.

SUMMARY

Methods and devices are provided for adjusting a basal delivery pattern according to the pharmacodynamics of insulin, to produce a transient basal profile. In some embodiments, a drug delivery device is provided and comprises the following: a drug delivery unit, a user interface adapted for receiving a desired change in basal rate, a processor adapted to adjust the desired change in basal rate with the pharmacodynamics of the delivered drug and accordingly provide an adjusted basal delivery profile. In some embodiments, the processor controls the drug delivery unit. In some embodiments, the adaptation of the processor comprises a processor having a basal programming application operating thereon.

In some embodiments, the drug delivery device includes a screen providing a graphical representation of the adjusted (transient) basal delivery profile to a user. In some embodiments, the drug delivery device is a skin securable insulin pump that can be remotely controlled.

The Adjusted Basal Rate (ABR, or "transient rate") is based on immediate, (and often times significant), administration of an over or under correction dose for a short period followed by a moderately modified dose for the remaining period of the transient change. At the end of the transient change period, an additional over or under correction may take place.

Examples of an ABR profile delivery include the following:

EXAMPLE 1

Transient basal rate (TBR)>current basal rate (CBR): a bolus is delivered immediately followed by a reduced basal delivery. For example:
CBR=1 U/h;
TBR=2 U/h;
change duration: 4 hours;
non-adjusted basal profile: 2 U/h for 4 hours (total. 8 U); and
adjusted basal profile: a bolus of 4 U is administered immediately followed by 1 U/h for 4 hours (e.g., total 8 U).

EXAMPLE 2

Transient basal rate (TBR)<current basal rate (CBR): basal delivery is reduced or stopped followed by an increased basal delivery. For example:
CBR—1 U/h;
TBR—0.6 U/h;
change duration: 4 hours;
non-adjusted basal profile: 0.6 U for 4 hours (e.g., total 2.4 U)
adjusted basal profile: basal delivery is stopped for 1 h followed by 0.8 U/h for 3 hours (e.g., total 2.4 U).

In some embodiments, if the desired transient basal rate (i.e., basal rate entered by the user is greater than a current basal rate (TBR>CBR), at least a portion of the additional basal insulin may be delivered as a bolus immediately at the beginning of the transient basal time period (for example).

In some embodiments, if the transient basal rate is less than the current basal rate (TBR<CBR), the basal rate may be significantly decreased or stopped (for example) for a short period of time immediately at the beginning of the transient basal time period.

In some embodiments, if TBR>CBR, at the end of the transient basal time period, the basal rate may be significantly decreased or stopped (for example) for a short period of time immediately before the end of the transient basal time period.

In some embodiments, if TBR<CBR, at the end of the transient basal time period, a bolus may be administered immediately before the end of the transient basal time period.

In some embodiments, the drug delivery device can further comprise a screen adapted for displaying the adjusted basal delivery profile.

The drug delivery device can also include a glucometer. In some embodiments, the drug delivery device comprises a remote control unit, and the glucometer is located in the remote control unit.

The drug delivery device can also comprise a dispensing patch unit, and the glucometer can be located in the dispensing patch unit. The drug delivery device can also comprise a continuous glucose monitor (CGM). In some embodiments, the continuous glucose monitor (CGM) is located in the dispensing patch unit.

In some embodiments, operation of the fluid delivery device can be carried out manually by operating buttons/switches (term used interchangeably throughout the present disclosure) located on the dispensing patch unit.

In some embodiments, the dispensing patch unit can be comprised of two parts: a disposable part and a reusable part. The disposable part can include a reservoir, outlet port and other inexpensive components, for example, while the reusable part can contain electronics (e.g., printed circuit board, processor, etc), driving mechanism(s) and other relatively expensive components.

In some embodiments, a cradle unit can be provided with the fluid delivery device. The cradle unit can be a substantially flat sheet or other structure that adheres to the skin and allows disconnection and reconnection of the patch unit thereto upon patient discretion. After attachment of the cradle unit to the skin, a cannula for insulin delivery can be inserted into a subcutaneous compartment of the patient through a dedicated passageway in the cradle unit, for example.

Some embodiments of the present disclosure provide a fluid delivery device that includes a skin securable dispensing patch unit composed of two parts. With such a device, a method for delivering an adjusted transient basal profile may be implemented. The dispensing patch unit may be attached to the skin directly, or by virtue of a cradle unit.

Some embodiments may provide a fluid delivery device comprising a dispensing patch unit that can be disconnected and reconnected to a patient, where the device may implement a method for delivering an adjusted transient basal profile. Some of these embodiments may provide a fluid delivery device comprising a miniature skin securable patch unit that can continuously dispense insulin and monitor body glucose concentration levels.

Some embodiments provide a fluid delivery device that is configured as an insulin infusion patch unit comprising a disposable part and a reusable part. The reusable part includes all relatively expensive components and the disposable part includes inexpensive components, thus providing a low cost product for the user and a highly profitable product for the manufacturer and user and/or insurer. The device may implement a method for delivering a drug to the user at a drug delivery rate in accordance with the adjusted transient basal delivery profile.

Some embodiments provide a fluid delivery device that comprises an insulin infusion patch unit that can be remotely controlled, where the device implements a method for delivering an adjusted transient basal profile.

In some embodiments, the user can accept an adjusted basal delivery pattern through the user interface, and accordingly, the user may be notified prior to basal profile change and either confirm or suspend the delivery or enter an alternative basal delivery profile.

A processor adapted/configured to adjust the desired change in basal rate can be implemented in a remote control unit and/or a reusable part of a skin securable dispensing patch.

The processor may be adapted to adjust the desired change in basal rate and can be implemented in a device that can continuously dispense insulin and monitor body glucose concentration levels and can dispense insulin according to glucose levels.

Thus, it is desirable to provide the ability to adjust a change in basal rate to establish a transient basal profile, so as to the delay in metabolic response, and can be implemented in one or more of the above-identified embodiments, as well as other embodiments described herein.

It is worth noting that the phrases "adapted to", "adapted for", "configured to", and "configured for", convey similar meanings to the structure for which they are used with herein, to accomplish a recited functionality.

A drug delivery system for administration of a therapeutic fluid (e.g., insulin) to the body of a patient at a transient basal delivery profile is disclosed herein. The system can comprise a user interface enabling input of one or more transient basal related parameters. The system includes a processor having a basal programming application operating thereon, the basal programming application configured for determining a transient basal profile based on at least the one or more transient basal related parameters, wherein the transient basal profile comprises a plurality of phases. In some embodiments, at least one of the plurality of phases includes either a basal overshot or a basal undershot. In some embodiments, the system includes a pump for dispensing the therapeutic fluid from a reservoir to the body of the patient. The basal programming application is used in conjunction with the processor for controlling the pump for dispensing the therapeutic fluid according to the transient basal profile.

In some embodiments, the basal overshot is characterized by at least a therapeutic fluid delivery rate substantially higher than the delivery rate in a steady state, and by a therapeutic fluid delivery duration substantially shorter than the delivery duration in a steady state.

In some embodiments, the basal undershot is characterized by at least a therapeutic fluid delivery rate substantially lower than the delivery rate in a steady state, and by a therapeutic fluid delivery duration substantially shorter than the delivery duration in a steady state.

According to some embodiments of the present disclosure, a steady state refers to a condition in which conventional transient basal profiles are determined, i.e., not including a plurality of phases and/or not including overshot(s) and/or undershot(s).

In some embodiments, the therapeutic fluid total dose corresponding to the transient basal profile determined by the basal programming application is substantially equivalent to a total dose delivered in a steady state. In other words, the area under the curve (AUC) of temporary basal delivery as known in the art is equivalent to the AUC of the adjusted transient basal profile determined by the basal programming application, whereas the temporal distribution of the fluid delivery of is different. The transient basal profile complies with the pharmacodynamics of the therapeutic fluid.

In some embodiments, the one or more transient basal related parameters can include one or more of time of transient delivery rate, percentage of transient delivery rate compared to the anticipated delivery profile, percentage of transient delivery rate compared to the current delivery profile, absolute value or values of a delivery rate, maximum allowable time shifted bolus, minimum allowable time shifted negative bolus, an absorption rate of the therapeutic fluid, type of therapeutic fluid, intensity of physical activity, and site of cannula insertion.

The system can further include a display (or screen) providing a graphical presentation of the transient basal profile. The transient basal profile can be displayed, for example, as at least one of: a table, diagram, graph, pie chart, xy graphs, ring chart, and bar chart.

In some embodiments, the user interface can include at least one of: keypad, keys, buttons, switches, voice commander, and touch-sensitive screen, and may be in communication (either wired or wireless) with the processor.

In some embodiments, the processor can be located in a remote control. In some embodiments, the processor can be located in the pump.

In some embodiments, the transient basal profile complies with pharmacokinetic and/or pharmacodynamic parameters of the therapeutic fluid.

In some embodiments, upon the transient basal profile including a transient basal rate which is greater than a normal basal rate, an immediate portion of the transient basal is delivered as a bolus.

In some embodiments, upon the transient basal profile including a basal rate which is less than a normal basal rate, an immediate portion of the transient basal is substantially reduced.

In some embodiments, upon the transient basal profile including a basal rate which is greater than a normal basal rate, a last portion of the transient basal is substantially reduced.

In some embodiments, upon the transient basal profile including a basal rate which is less than a normal basal rate, a last portion of the transient basal delivered as a bolus.

Embodiments of the system may include any one or more of the features described above in relation to the fluid dispensing device and/or method disclosed herein as well as one or more of the following features.

A method for adjusting a transient basal delivery profile for a therapeutic fluid delivered to the body of a patient is disclosed. The method comprises providing a therapeutic fluid dispensing device, the device including a user interface enabling input of one or more transient basal related parameters; a processor having a basal programming application operating thereon; and a pump dispensing the therapeutic fluid from a reservoir to the body of a patient; receiving, via the user interface, the one or more transient basal related parameters; determining, via the basal programming application, a transient basal profile based on at least the one or more transient basal related parameters, wherein the transient basal profile comprises a plurality of phases and wherein at least one of the plurality of phases includes either a basal overshot or a basal undershot.

In some embodiments, the method may further comprise controlling, via the basal programming application used in conjunction with the processor, the pump for dispensing the therapeutic fluid according to the transient basal profile.

In some embodiments, determining the one or more transient basal related parameters includes determining a therapeutic fluid delivery rate substantially higher than the delivery rate in a steady state; and determining a therapeutic fluid delivery duration substantially shorter than the delivery duration in a steady state.

In some embodiments, determining the one or more transient basal related parameters includes determining a therapeutic fluid delivery rate substantially lower than the delivery rate in a steady state; and determining a therapeutic fluid delivery duration substantially shorter than the delivery duration in a steady state.

In some embodiments, for example the noted embodiments referred to above, "determining" may comprising "receiving" in one or more instances.

In some embodiments, the therapeutic fluid total dose corresponding to the transient basal profile determined by the basal programming application is substantially equivalent to a total dose delivered in a steady state.

In some embodiments, the one or more transient basal related parameters can be one of: time of transient delivery rate, percentage of transient delivery rate compared to the anticipated delivery profile, percentage of transient delivery rate compared to the current delivery profile, absolute value or values of a delivery rate, maximum allowable time shifted bolus, minimum allowable time shifted negative bolus, an absorption rate of the therapeutic fluid, type of therapeutic fluid, intensity of physical activity, and site of cannula insertion.

In some embodiments, the method further comprising displaying the transient basal delivery profile to a user.

In some embodiments, the transient basal delivery profile further comprises at least one additional basal profile to be delivered during at least one additional basal duration.

In some embodiments, the method further comprises administering the therapeutic fluid, and wherein such administration complies with pharmacokinetic and/or pharmacodynamic parameters of the therapeutic fluid.

Embodiments of the method may include any one or more of the features described above in relation to the fluid dispensing system and/or methods disclosed herein as well as one or more of the following features.

A method for adjusting a basal delivery profile is disclosed. The method comprises receiving, by at least one of a drug delivery device and any remote control device thereof, a desired basal delivery profile for delivery of a drug to a user; and adjusting the basal delivery profile to a transient basal profile, wherein the transient basal profile includes at least two basal rates.

In some embodiments, upon the transient basal profile including a transient basal rate which is greater than a normal basal rate, an immediate portion of the transient basal is delivered as a bolus.

In some embodiments, upon the transient basal profile including a basal rate which is less than a normal basal rate, an immediate portion of the transient basal is substantially reduced.

In some embodiments, upon the transient basal profile including a basal rate which is greater than a normal basal rate, a last portion of the transient basal is substantially reduced.

In some embodiments, upon the transient basal profile including a basal rate which is less than a normal basal rate, a last portion of the transient basal delivered as a bolus.

In some embodiments, the method further comprising setting a maximum delivery dose comprising an immediate portion of the transient basal profile.

In some embodiments, the method further comprising setting a minimum delivery dose comprising an immediate portion of the transient basal profile.

In some embodiments, the method further comprising setting a maximum delivery dose comprising a last portion of the transient basal profile.

In some embodiments, the method further comprising setting a minimum delivery dose comprising a last portion of the transient basal profile.

Embodiments of the method may include any one or more of the features described above in relation to the fluid dispensing system and/or methods disclosed herein as well as one or more of the following features.

A method for adjusting a transient basal delivery profile of a therapeutic fluid is disclosed. The method comprises receiving, by at least one of a drug delivery device and any remote control thereof, a first basal profile comprising a first basal rate and first basal duration; receiving, by at least one of the drug delivery device and any remote control thereof, a second basal profile comprising a second basal rate and a second basal duration, wherein the first and second basal profiles correspond to a transient basal profile; and adjusting the transient basal profile to deliver the first basal rate during the first basal duration, and subsequently delivering the second basal rate during the second basal duration.

In some embodiments, the method can further comprise administering the therapeutic fluid according to the transient basal delivery profile.

In some embodiments of the present disclosure, a method and/or device to control delivery of fluid to the body of a patient using the above mentioned system is described.

A drug delivery device for administration of a therapeutic fluid to the body of a patient at a transient basal delivery profile is disclosed. The device comprises means for interfacing with a user for enabling input of one or more transient basal related parameters; basal programming means configured for determining a transient basal profile based on at least the one or more transient basal related parameters, wherein the transient basal profile comprises a plurality of phases and wherein at least one of the plurality of phases includes either a basal overshoot or a basal undershoot.

In some embodiments, the device further comprises pumping means for dispensing the therapeutic fluid from a reservoir to the body of the patient; the basal programming means controls the pumping means for dispensing the therapeutic fluid according to the transient basal profile.

Embodiments of the device may include any one or more of the features described above in relation to the fluid dispensing system and/or methods disclosed herein as well as one or more of the following features.

A method for determining a a transient basal delivery profile is disclosed. The method comprises setting at least one of an overshoot or an undershoot; determining a transient basal profile including a plurality of phases, the at least one of the plurality of phases includes at least one of the overshoot and undershoot.

In some embodiments, the method further comprises displaying the basal delivery profile to a user.

In some embodiments, the method further comprises storing the transient basal profile.

In some embodiments, the method further comprises communicating the transient basal profile to a device. Communicating may be carried out, for example, via wires or wirelessly.

Embodiments of the method may include any one or more of the features described above in relation to the fluid dispensing system, device and/or methods disclosed herein as well as one or more of the following features.

In some embodiments, a medical device is provided. In some variations, the medical device can implement the method for adjusting a transient basal delivery profile for a therapeutic fluid delivered to the body of a patient. For example, the medical device can comprise a tangible machine-readable storage medium embodying instructions that when performed by one or more processors result in operations comprising: receiving one or more transient basal related parameters; determining a transient basal profile based on at least the one or more transient basal related parameters, wherein the transient basal profile comprises a plurality of phases and wherein at least one of the plurality of phases includes either a basal overshoot or a basal undershot.

In some embodiments, the medical device can include a user interface enabling input of the one or more transient basal related parameters, and a pump dispensing the therapeutic fluid from a reservoir to the body of a patient according to the transient basal profile.

Embodiments of the medical device may include any one or more of the features described above in relation to the fluid dispensing system, device and/or methods disclosed herein as well as one or more of the following features.

DETAILED DESCRIPTION

Figure 1A:
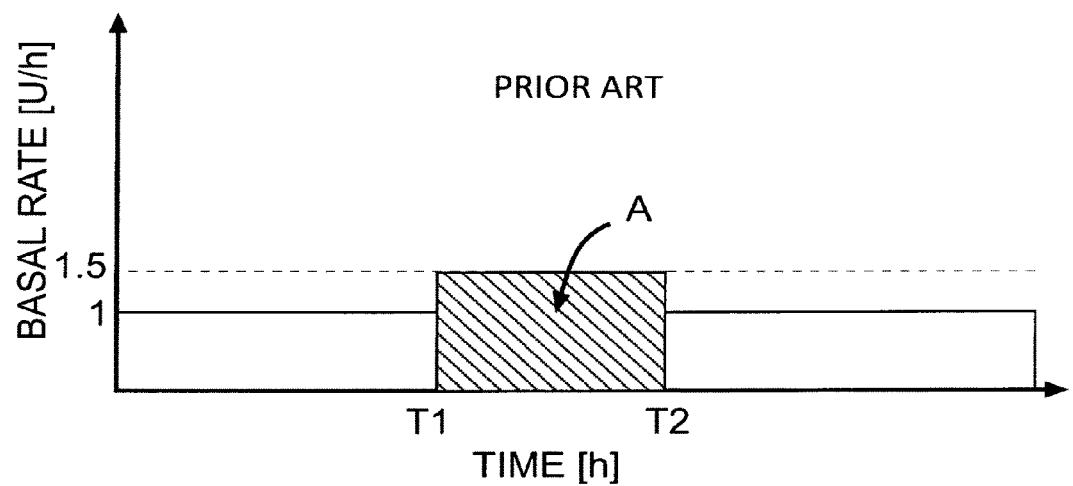
FIG. 1a illustrates a basal delivery profile which includes an increased transient basal delivery rate change (A) for a predefined time period (T1 to T2), known to one skilled in the art.

FIG. 1a is an exemplary graph representing a basal delivery profile including a transient change in basal delivery rate for a predefined period as has been provided by conventional insulin pumps. As illustrated in FIG. 1a, the user's/patient's basal rate is 1 U/h and a transient basal rate (designated as "A") of 1.5 U/h is set during a time period marked between "T1" and "T2".

Figure 1B:
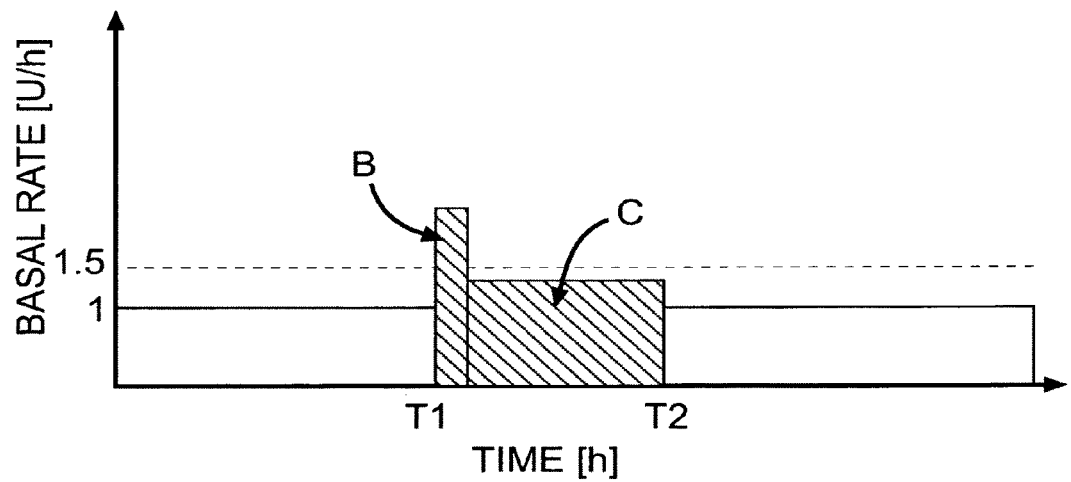
FIG. 1b illustrates an increased transient basal delivery rate change (B and C) for a predefined time period (T1 to T2), according to some embodiments of the present disclosure.

FIG. 1b is an exemplary graph representing a basal delivery profile including a transient change in basal delivery rate according to a method disclosed herein of some of the embodiments of the present disclosure. As illustrated in FIG. 1a, the basal rate is 1 U/h and the desired transient basal rate corresponds to 1.5 U/h during a time period of T1 to T2 (for example). Typically, conventional insulin transient basal administration (as show in FIG. 1a for example) may not overcome blood glucose deviations due to, for example, a lag in insulin absorption and delayed pharmacokinetics and/or pharmacodynamics. In order to provide a basal delivery rate (e.g., 1.5 U/h) for that period of time (T1 to T2) which complies with the pharmacodynamics of insulin (e.g., the delayed physiological response), a portion of the transient basal (B) is delivered immediately at T1 (may be equivalent to a bolus dose, also referred to "insulin basal overshoot", consisting of insulin dose greater than that which would have been administered in a steady-state, as illustrated in FIG. 1a for example), followed by a complementary reduced dose (C) administered during the remaining period. This "time-shifted" transient basal delivery dose, i.e., the part of the transient basal insulin that is delivered immediately at T1 as a "bolus" rather than continuously over the entire transient time period, enables rapid basal rate stabilization, that is, a reduction or even an elimination of the delayed response.

Figure 2A:
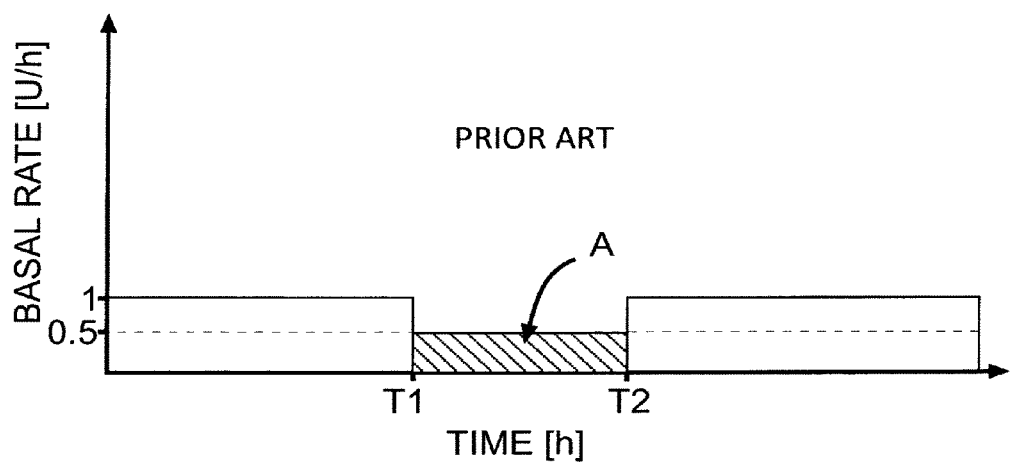
FIG. 2a illustrates a basal delivery profile which includes a decreased transient basal delivery change (A) for a predefined time period (T1 to T2), known to one skilled in the art.
Figure 2B:
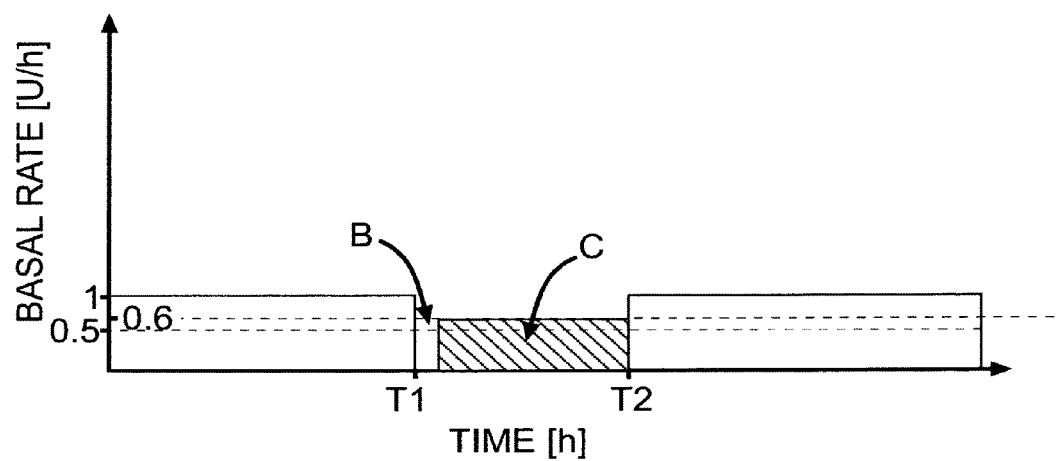
FIG. 2b illustrates a decreased transient basal delivery rate change (B and C) for a predefined time period (T1 to T2), according to some embodiments of the present disclosure.

According to some embodiments, the amount of delivered insulin is maintained given the change of the transient basal profile noted above—the area under the curve (AUC) of temporary basal delivery of insulin as known in the art and depicted in FIGS. 1a and 2a (marked as 'A' is equivalent to the AUC of the adjusted transient basal profile, marked as 'B' and 'C' in FIGS. 1b and 2b). However, the temporal distribution of the insulin delivery is different, and complies with the pharmacodynamics of insulin (e.g., compensating delayed insulin absorption and/or delayed activation of insulin within the body).

In some embodiments, the first phase (B) is characterized by a rate substantially higher than the rate of the second phase (C), and by a time period substantially shorter than the time of the second phase (C).

According to some embodiments, the amount and duration of the adjusted transient doses (e.g. 'B' and 'C' in FIGS. 1b and 2b) can be automatically set, for example, as a percentage of the current basal rate (CBR) or, in some embodiments, as a pre-set value. For example, for an increase of basal rate by 50% (e.g. from 1 U/h to 1.5 U/h) for 4 hours, the adjusted transient basal delivery profile may include the following parameters:

a first phase (B) characterized by a first TBR of 2 U/h (which are 100% increase of the CBR) and a duration of 1 hour (which is 25% of the total time period of the transient basal delivery profile), and a second phase (C) characterized by a second TBR of 1.33 U/h (which are 33% reduction of the CBR) and a duration of 3 hours (which are 75% of the total time period).

Thus, in the above-noted example, the total dose of delivered insulin during the transient basal delivery change is 6 U (i.e. 2 U/h×1 h+1.33 U/h×3 h), which is equivalent to the dose of constant delivery of 1.5 U/h for 4 h (1.5 U/h×4 h). It is important to mention that even though these two profiles are equivalent in the insulin dose administered, their affect on glucose level is different because of their temporal distribution over time.

According to some embodiments, the user or caregiver can set (e.g., initially) maximum or minimum values for doses that can be delivered during the adjusted transient basal delivery profile.

According to some embodiments, a transient basal delivery profile can comprise a plurality of phases (e.g., 2, 3 and 5 phases), where each phase is characterized by specific dose and duration. The profile and its phases can include various curve types such as "step-like" curve (depicted in FIGS. 1a-2b), polynomial, triangular, sinusoidal or representing any other mathematical function or empirical behavior. A change (e.g., increase or decrease) in basal delivery rate may also be gradual or smooth (unlike as shown in FIGS. 1a-2b).

According to some embodiments, the transient delivery profile can be based on one or more of the following parameters (for example), which may be entered by the user and/or caregiver: an absorption rate of the therapeutic fluid, type of therapeutic fluid (e.g., rapid acting insulin, regular insulin), intensity of physical activity and/or site of cannula insertion.

FIG. 2a is another exemplary graph representing a basal infusion rate including a transient basal delivery change, implemented in currently available insulin pumps. As shown, the basal rate is 1 U/h and a transient basal rate is set during a time period marked between 'T1' and 'T2', to be at 0.5 U/h. Such conventional insulin transient basal administration may not overcome blood glucose deviations due to, for example, lag in insulin absorption and delayed pharmacokinetics and/or pharmacodynamics.

FIG. 2b is an exemplary graph representing a current basal delivery rate and a transient basal delivery rate according to some embodiments of the present disclosure, which illustrates the delivery of an equivalent dose of insulin to that depicted in FIG. 2a (i.e., 0.5 U/h from T1 to T2). In order for the delivery rate of 0.5 U/h to comply/synchronize with the pharmacodynamics of insulin (e.g., a delayed response), a portion of the adjusted transient basal delivery (B) can be significantly reduced, followed by administration of an adjusted dose (C). In the given example (shown in FIG. 2b), the immediate portion (B, also referred-to as "first phase") of the transient basal is reduced to substantially 0 U/h, followed by administration of 0.6 U/h (C, also referred-to as "second phase") for the remaining time of the transient basal delivery. In the case of a transient basal profile which is less than the current basal rate, the immediate portion of the transient basal is time shifted to implement a significantly reduced delivery rate for a relatively short time period (hereinafter known as "negative bolus" or "insulin basal undershoot", consisting of a dose less than that which would have been administered in a steady-state, as shown in FIG. 2a for example), and so enables rapid basal rate stabilization. That is, a part of the transient basal insulin is delivered immediately at T1 as a "negative bolus" rather than continuous reduction of the basal rate over the entire transient time period. Such a "negative bolus", according to some embodiments, may therefore constitute a period of time that no insulin is delivered to the user.

In some embodiments, the first phase (B) is characterized by a rate substantially lower than the rate of the second phase (C), and by a time period substantially shorter than the time of the second phase (C).

According to some embodiments, the AUC of the transient basal delivery known in the art (marked as 'A' in FIG. 2a), is equivalent to the AUC of the adjusted transient basal delivery profile (marked as 'B' and 'C' in FIG. 2b).

According to some embodiments, the portion of the "negative bolus" of the transient basal insulin (e.g. designated with the letter 'B' in FIG. 2b) can be automatically set (i.e., without user interface). For example, it can be set as a percentage of the total transient insulin or as a pre-set value. The user or caregiver can initially set a minimum value that can be delivered as a "negative bolus" portion. Alternatively the "negative bolus" portion can be set by the user.

Figure 3:
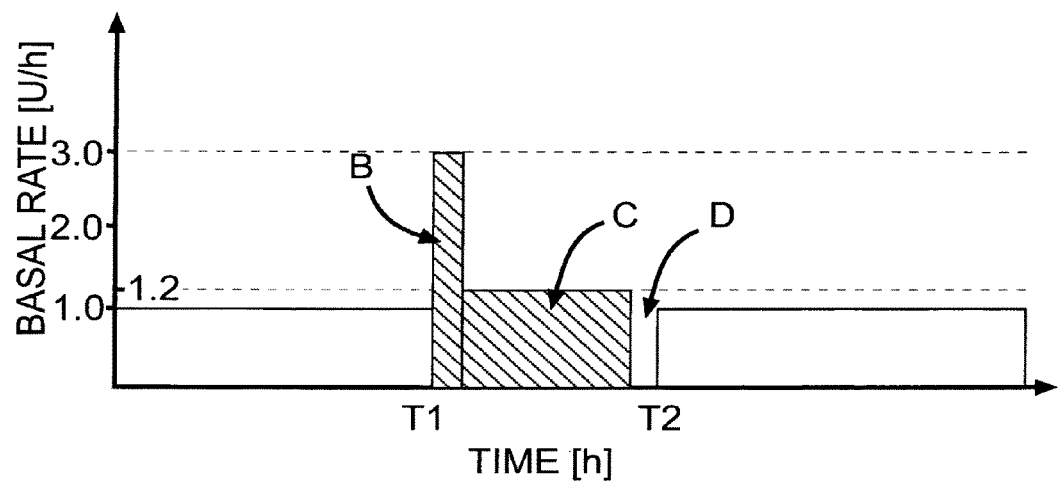
FIG. 3 illustrates another basal delivery profile which includes a transient basal deliver rate change, according to some embodiments of present disclosure.

FIG. 3 illustrates yet another embodiment of an adjusted transient basal delivery profile, according to some embodiments of the present disclosure. In this example, the current basal delivery rate is 1 U/h and the desired TBR is 1.5 U/h (as depicted FIG. 1a). In order for the desired delivery rate of 1.5 U/h to synchronize with the delayed pharmacodynamics of insulin, a portion of the transient basal is delivered immediately as a bolus ('B', i.e. 3 U/h) followed by a reduced dose ('C', i.e. 1.2 U/h). This "time-shifted" transient basal insulin enables rapid basal rate stabilization. In order for the basal rate to reach the desired normal value (the value to be reached by the end of the transient basal delivery change, time T2, i.e., 1 U/h in the given example) as soon as possible, the last portion of the adjusted transient basal rate period is time shifted backwards to create a "negative bolus" ('D', i.e., 0 U/h).

According to some embodiments, the AUC of the transient basal delivery as described in prior art (marked as A in FIG. 1a) is equivalent to the AUC of the adjusted transient basal delivery (marked as 'B', 'C' and 'D' in FIG. 3).

According to some embodiments, the portion of the time shifted transient basal insulin (i.e., designated with the letter 'B' in FIG. 3) and the portion of the 'negative bolus' of the transient basal insulin (i.e., designated with the letter 'D' in FIG. 3) can be automatically set (for example). It can be set as a percentage of the total insulin and/or as a pre-set value. For example, the user or caregiver can initially set a maximum value that can be delivered as a time shifted transient basal and a minimum value that can be delivered as a 'negative bolus'. Alternatively, the time shifted transient basal insulin and the 'negative bolus' can be set by the user.

Figure 4:
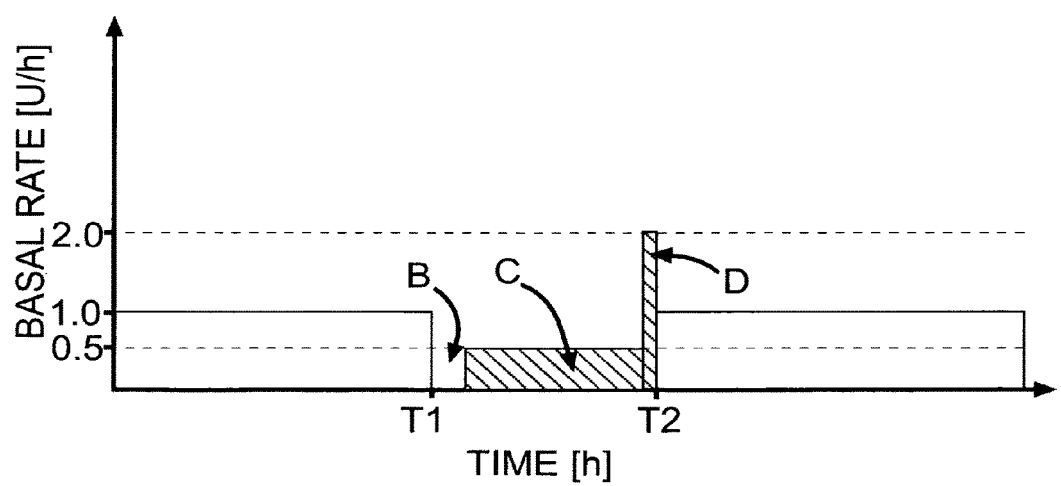
FIG. 4 illustrates another basal delivery profile which includes a transient basal deliver rate change, according to some embodiments of present disclosure.

FIG. 4 shows another embodiment of adjusted transient basal delivery according to the method of the current disclosure. In this example, the current basal delivery rate is 1 Uh and the desired transient rate is 0.5 U/h (as shown in FIG. 2a). In order for the desired delivery rate of 0.5 U/h to synchronize with the delayed pharmacodynamics of insulin, the delivery of the transient basal is postponed so the immediate transient delivery is significantly reduced or stopped. In the given example, the immediate portion of the transient basal is reduced to 0 U/h ('B'). The immediate portion of the transient basal is time shifted to create a "negative bolus" and so enables rapid transient basal rate stabilization. In order for the basal rate to reach the desired normal value, that is, the value to be reached by the end of the transient basal delivery change, time T2 (i.e., 1 U/h in the given example), as soon as possible, the last portion of the transient basal rate is delivered as a bolus ('D', i.e., 2 U/h).

According to some embodiments, the AUC of the transient basal delivery as described in prior art (marked as A in FIG. 2a) is equivalent to the AUC of the adjusted transient basal delivery profile (marked as 'B', 'C' and 'D' in FIG. 4).

Figure 5:
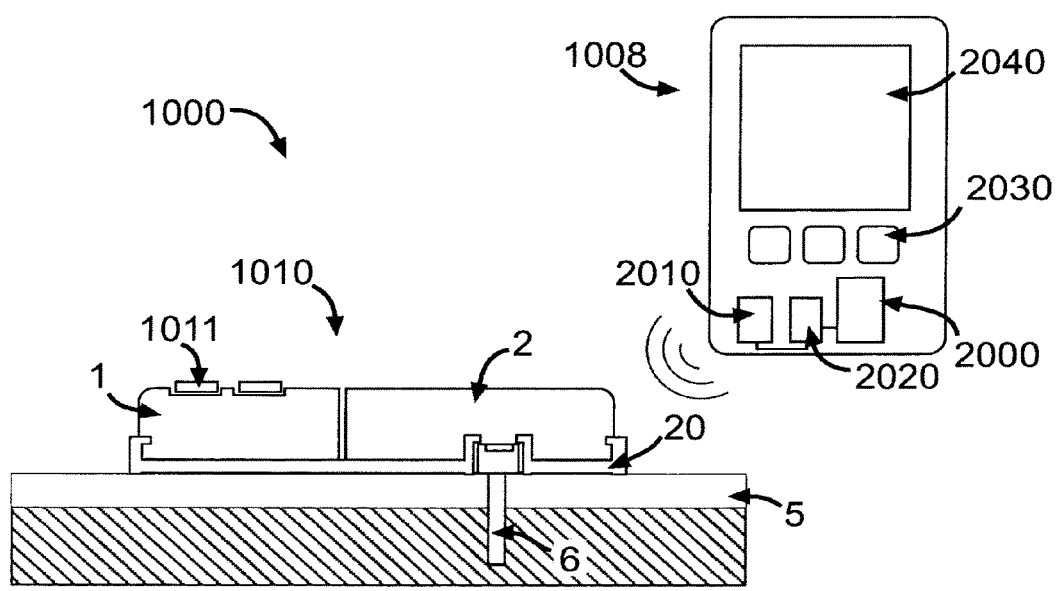
FIG. 5 illustrates an insulin infusion device comprising a skin adherable dispensing unit and a remote control unit. The device includes a processor adapted to adjust the desired basal rate change, according to some embodiments of the present disclosure.

FIG. 5 shows an embodiment of a fluid delivery device/system, e.g., an insulin infusion device (1000) comprising a dispensing patch unit (1010), also referred-to as "patch unit" or "patch" or "dispensing unit" or "pump", and a remote control unit (1008) (or "remote control"), which can communicate with the dispensing patch unit (1010), enabling (for example) programming, user inputs and data acquisition. In some embodiments, the remote control unit may be implemented in a Personal Data Assistance (PDA), a cellular phone, a watch, an iPod (i.e., a media player), an iPhone, iPad, a laptop and/or a PC.

The patch unit (1010) can be detachably removable from the skin (5) of a user. In some embodiments, the patch unit (1010) can be attached to the skin or to a skin adherable cradle unit (20) which enables connection and disconnection of the patch unit (1010) to and from the cradle unit (20). A cannula (6) is inserted through an opening of the cradle and connected (preferably rigidly) to the cradle after insertion. Connection of the patch (1010) to the cradle (20) establishes fluid communication between a reservoir, located within the patch, and the cannula.

An example of such a patch unit is disclosed in co-owned U.S. patent publication no. 20070106218 and international patent application No. PCT/IL09/000388, the disclosures of which are herein incorporated by reference in their entireties.

An exemplary embodiment of the cradle is disclosed in co-owned U.S. patent publication no. 20080215035 and international patent application no. PCT/IL07/001578, the disclosures of which are herein incorporated by reference in their entireties.

Manual inputs for operating and controlling the dispensing patch unit can be carried out by one or more buttons or switches (1011) located on the dispensing patch unit (1010). In some embodiments, the dispensing patch unit (1010) can be comprised of a single part or of two parts: a reusable part (1) and a disposable (2) part.

In some embodiments, the remote control unit (1008) may contain a basal programming feature (2000) for adjustment of transient basal delivery profile, a programmable processor (2010), a memory (2020), a keypad (2030) or any other input means (e.g., buttons, switches, touch-screen, voice commander), a display/screen (2040) and/or other notification means such as audible (e.g. buzzer) and/or vibration (e.g. vibrator) means, to notify the user. The keypad (2030) and input means can be used for programming and commanding the dispensing patch unit (1010) and the basal programming feature (2000).

In some embodiments, the basal programming feature can suggest or recommend to the user a transient basal rate profile that complies with the pharmacodynamics of insulin.

According to some embodiments, the basal programming feature can be located in the patch unit (e.g. in the reusable part). In some embodiments, the basal programming feature can be shared between the remote control unit and the dispensing patch unit.

Figure 6A:
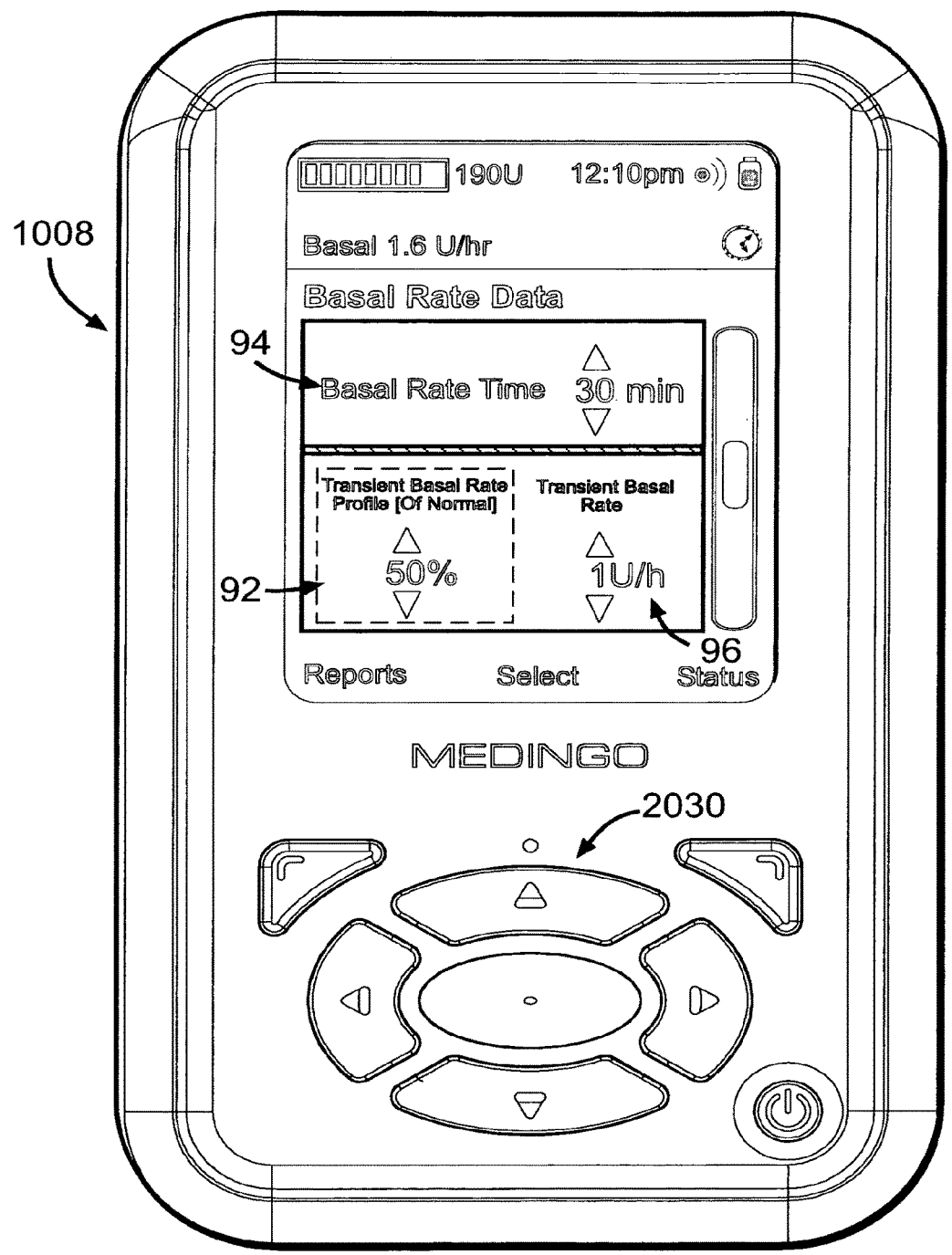
FIGS. 6a-b provide examples of a user interface for adjustment of the transient basal delivery profile, according to some embodiments of the present disclosure.
Figure 6B:
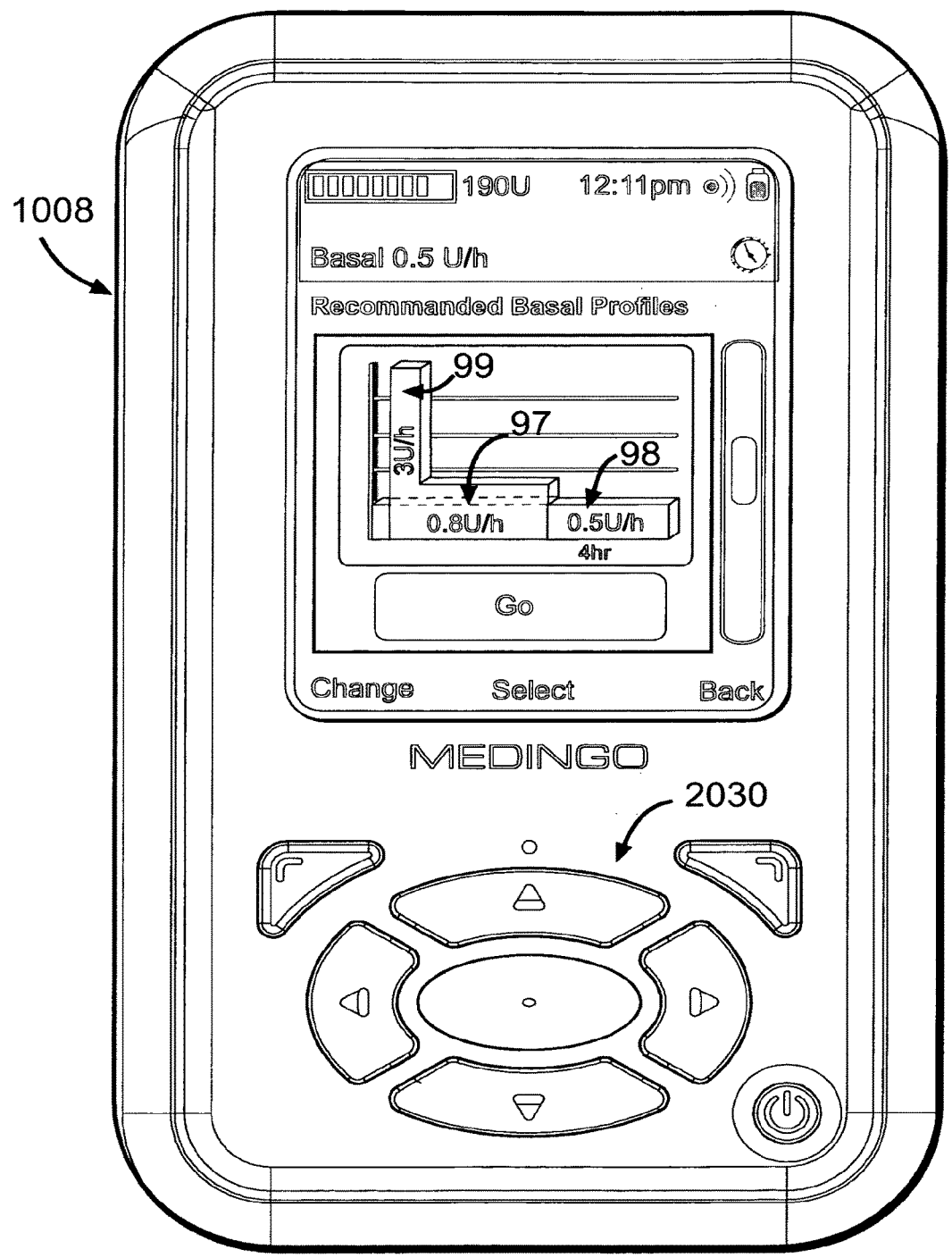

FIGS. 6a-b provide an example of a user interface presented by a screen/display implemented by the basal programming feature. The screen/display may be located at the remote control unit (1008) at the dispensing patch unit and at both units. An example for a patch unit including a screen is disclosed in co-owned International Patent Application No. PCT/IL2008/001057, the disclosure of which is incorporated by reference in its entirety.

FIG. 6a illustrates an example of a window of the user interface in which the user can input (e.g. enter or select) the desired adjusted transient basal rate. For example, the user can input a value (e.g. 0.5 U/h) of basal rate (96) or a percentage (e.g. 50%) of a current rate (92). In some embodiments, the value can be a discrete value or a range of values. The user can also input duration (e.g. 30 minutes) of the adjusted transient basal rate (94). In some embodiments, the input values can be inputted from external database and/or device such as website or a PC.

FIG. 6b illustrates an example of a graphical user interface (GUI) of an adjusted transient basal profile according to some embodiments of the disclosure.

In the given example, the current profile is 0.5 U/h (98). The user inputted a transient basal rate of 1 U/h and the recommended adjusted transient basal profile comprises an immediate dose (first phase) of 3.0 U/h (99) followed by a second phase of 0.8 U/h (97). In some embodiments, when the transient basal profile terminates, the basal rate may return to be the current basal rate (manually or automatically), or in other embodiments, a new basal rate can be inputted.

Figure 7A:
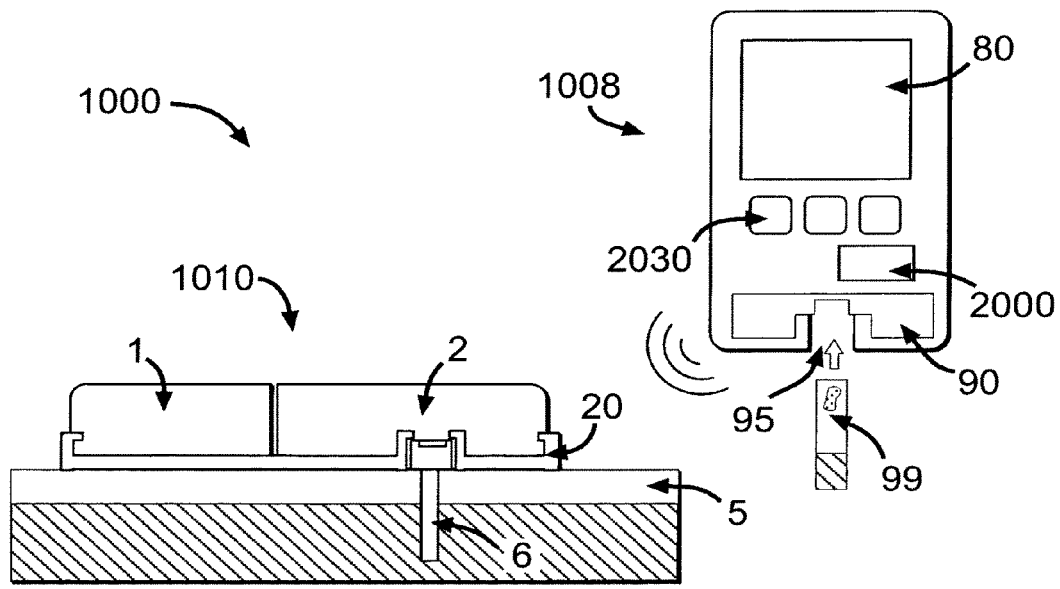
FIGS. 7a-c illustrate different embodiments of an insulin infusion device that comprises an insulin dispensing unit, a remote control unit, a blood glucose monitor, and a processor adapted to adjust the desired basal rate change.
Figure 7B:
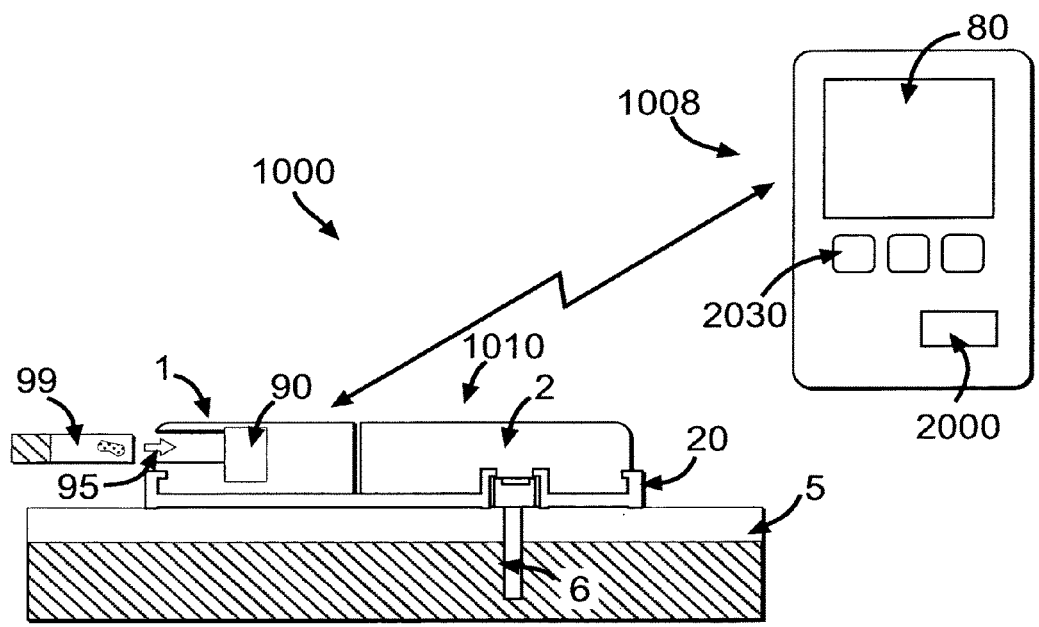
Figure 7C:
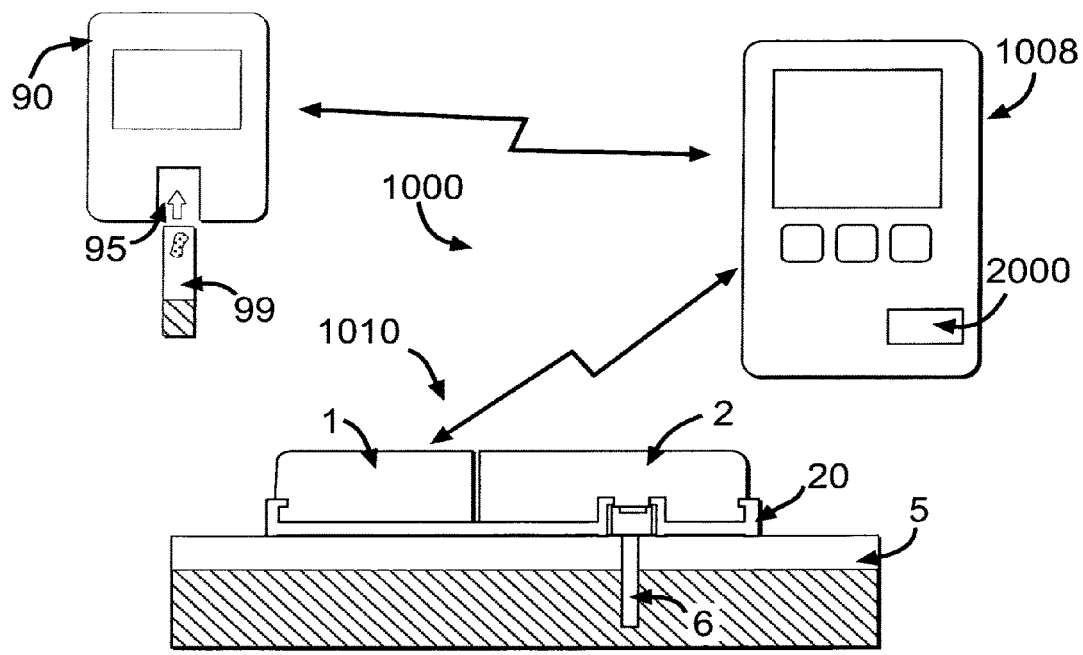

FIGS. 7a-c provide embodiments of a drug delivery device/system, e.g., an insulin infusion device. In these embodiments, the device/system comprises an insulin dispensing unit, a remote control unit that can be provided with a basal programming feature (2000), and a sensor glucose levels monitoring (e.g. glucometer).

FIG. 7a illustrates a glucometer (90) located in the remote control unit (1008) of the system. The glucometer (90) may comprise a device/system for determining blood glucose levels (familiar to those of skill in the art), and in some embodiments, includes an opening (95) for receiving of a test strip (99). The user extracts blood from the body, places a blood drop on the test strip (99) and inserts the strip (99) into the opening (95). The glucose readings (e.g. glucose concentration) can then be determined and displayed on a screen (80) of the remote control unit (1008). In some embodiments, the glucose readings can be restored in a memory located in the remote control and can be transmitted to another device such as the dispensing unit or PC.

FIG. 7b illustrates the dispensing unit configured as a dispensing unit (1010) having reusable part (1) and a disposable part (2), according to some embodiments. The dispensing unit (1010) may include a glucometer (90) located in the reusable part (1).

In some embodiments, glucose readings can be directly or remotely received (by the patch unit (1010) or remote control unit (1008) from the glucometer (90), a "stand-alone" device, as illustrated in FIG. 7c. Communication can be also carried out between glucometer and patch indicated by the Z-arrow.

Figure 8A:
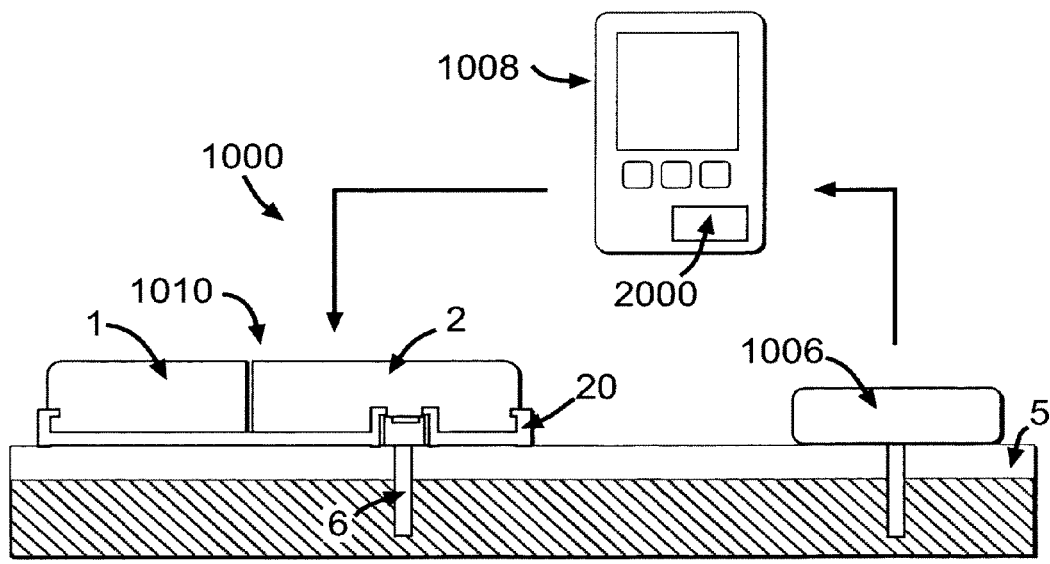
FIGS. 8a-b illustrate different embodiments of a system/device that comprises an insulin infusion device and a continuous subcutaneous glucose monitor, and a processor adapted to adjust the desired basal rate change.
Figure 8B:
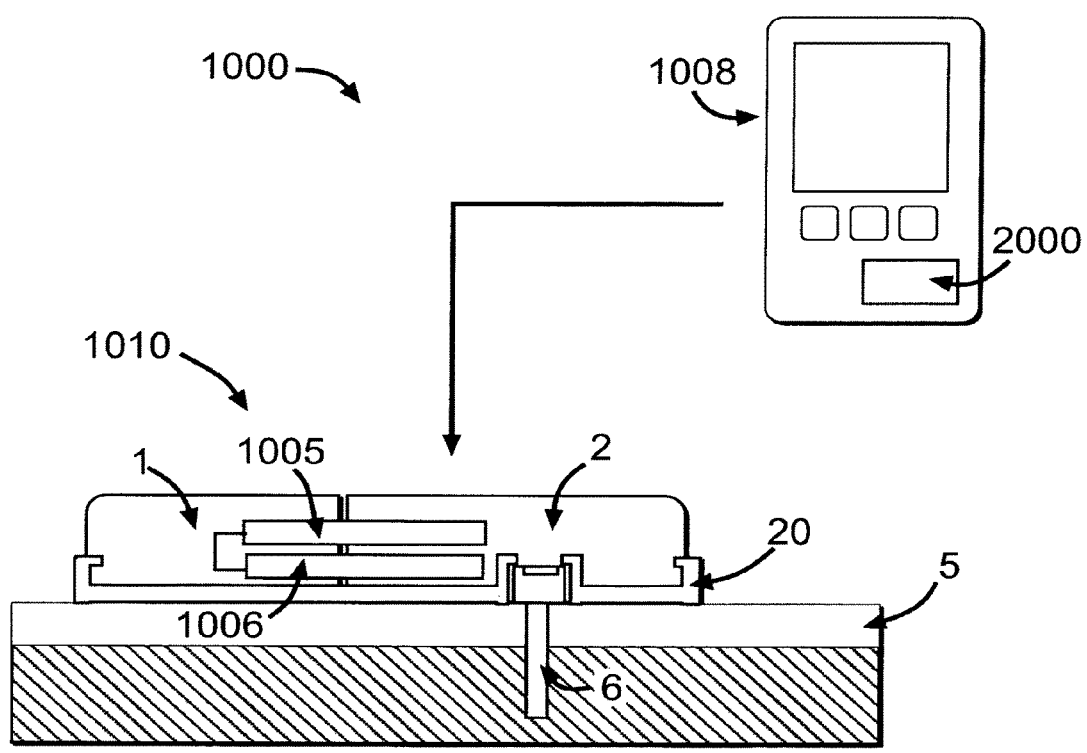

FIGS. 8a-b illustrate embodiments of a drug delivery device/system, e.g., an insulin infusion system which may include an insulin dispensing unit (1010), a remote control unit (1008) that can be provided with a basal programming feature (2000), and a subcutaneous continuous glucose monitor (CGM) (1006).

FIG. 8a illustrates a "stand-alone" CGM (1006).

FIG. 8b illustrates an integrated device/system in which the CGM (1006) is located within the dispensing patch unit (1010). An example of such an integrated device/system is disclosed in co-owned U.S. publication nos. 20070191702 and 20080214916, and in international patent applications nos. PCT/IL2007/001579 and PCT/IL2008/001521, the disclosures of which are herein incorporated by reference in their entireties.

Various embodiments of the basal programming application described herein may be realized in digital electronic circuitry, integrated circuitry, specially designed ASICs (application specific integrated circuits), computer hardware, firmware, software, and/or combinations thereof. These various embodiments may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. For example, this program can be stored, executed and operated by the dispensing unit, remote control, PC, laptop or personal data assistant ("PDA"). Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other. For example, a patient that does not have his remote control unit "at arm's length", can administer and control a bolus dose administration via the internet. Another implementation refers to a physician that is located far from the patient and device, but still able to monitor, operate and receive data from the device via the internet or a data server, e.g., a U.S. based physician can communicate with the device and patient which are situated overseas.

Some embodiments of the present disclosure preferably implement the basal programming application via software operated on a processor contained in a remote control device of an insulin dispensing system and/or a processor contained in a insulin dispensing device being party of an insulin dispensing system.

Any and all references to publications or other documents, including but not limited to, patents, patent applications, articles, webpages, books, etc., presented in the present application, are herein incorporated by reference in their entireties.

Although a few variations have been described in detail above, other modifications are possible. For example, any logic disclosed in the present disclosure does not require the particular order shown, or sequential order, to achieve desirable results. Other embodiments are possible, some of which, are within the scope of the following claims.

What is claimed is:

1. A method for adjusting a transient basal delivery profile for a therapeutic fluid delivered to the body of a patient, the method comprising:
   providing a therapeutic fluid dispending device, the device including:
   an input to receive one or more transient basal related parameters;
   a processor having a basal programming application operating thereon; and
   a pump dispensing the therapeutic fluid from a reservoir to the body of a patient;
   receiving, via the input, the one or more transient basal related parameters;
   determining, via the basal programming application, a transient basal profile based on at least the one or more transient basal related parameters, wherein the transient basal profile comprises two or more phases and wherein at least one of the two or more phases includes either a basal overshot or a basal undershot.

2. The method of claim 1, further comprising controlling, via the basal programming application used in conjunction with the processor, the pump for dispensing the therapeutic fluid according to the transient basal profile.

3. The method of claim 1, wherein determining the one or more transient basal related parameters includes:
   determining a therapeutic fluid delivery rate substantially higher than the delivery rate in a steady state; and
   receiving a therapeutic fluid delivery duration substantially shorter than the delivery duration in a steady state.

4. The method of claim 1, wherein determining the transient basal profile based on at least the one or more transient basal related parameters includes:
   determining a therapeutic fluid delivery rate substantially lower than the delivery rate in a steady state; and
   determining a therapeutic fluid delivery duration substantially shorter than the delivery duration in a steady state.

5. The method of claim 1, wherein the therapeutic fluid total dose corresponding to the transient basal profile determined by the basal programming application is substantially equivalent to a total dose delivered in a steady state.

6. The method of claim 1, wherein the one or more transient basal related parameters is selected from a group consisting of time of transient delivery rate, percentage of transient delivery rate compared to the anticipated delivery profile, percentage of transient delivery rate compared to the current delivery profile, absolute value or values of a delivery rate, maximum allowable time shifted bolus, minimum allowable time shifted negative bolus, an absorption rate of the therapeutic fluid, type of therapeutic fluid, intensity of physical activity, and site of cannula insertion.

7. The method of claim 1, further comprising displaying the transient basal delivery profile to a user.

8. The method of claim 1, wherein the transient basal delivery profile further comprises at least one additional basal profile to be delivered during at least one additional basal duration.

9. The method of claim 1, further comprising administering the therapeutic fluid, and wherein such administration complies with pharmacokinetic and/or pharmacodynamic parameters of the therapeutic fluid.

10. The method of claim 1, wherein the receiving, via the input, of the one or more transient basal related parameters is from a remote control unit, a sensor, a glucometer or a continuous glucose monitor.

11. A computer program comprising computer-executable instructions, which when executed on a suitable computer device, perform the method comprising:
    receiving, via an input, one or more transient basal related parameters;

determining, via a basal programming application, a transient basal profile based on at least the one or more transient basal related parameters, wherein the transient basal profile comprises two or more phases and wherein at least one of the two or more phases includes either a basal overshot or a basal undershot.

12. The computer program of claim 11, wherein the method further comprises controlling, via the basal programming application used in conjunction with the processor, the pump for dispensing the therapeutic fluid according to the transient basal profile.

13. The computer program of claim 11, wherein receiving, via the input, of the one or more transient basal related parameters is from a remote control unit, a sensor, a glucometer or a continuous glucose monitor.

14. The computer program of claim 11, wherein determining the one or more transient basal related parameters includes:
  determining a therapeutic fluid delivery rate substantially higher than the delivery rate in a steady state; and
  receiving a therapeutic fluid delivery duration substantially shorter than the delivery duration in a steady state.

15. The computer program of claim 11, wherein determining the transient basal profile based on at least the one or more transient basal related parameters includes:
  determining a therapeutic fluid delivery rate substantially lower than the delivery rate in a steady state; and
  determining a therapeutic fluid delivery duration substantially shorter than the delivery duration in a steady state.

16. The computer program of claim 11, wherein the therapeutic fluid total dose corresponding to the transient basal profile determined by the basal programming application is substantially equivalent to a total dose delivered in a steady state.

17. The computer program of claim 11, wherein the one or more transient basal related parameters is selected from a group consisting of: time of transient delivery rate, percentage of transient delivery rate compared to the anticipated delivery profile, percentage of transient delivery rate compared to the current delivery profile, absolute value or values of a delivery rate, maximum allowable time shifted bolus, minimum allowable time shifted negative bolus, an absorption rate of the therapeutic fluid, type of therapeutic fluid, intensity of physical activity, and site of cannula insertion.

18. The computer program of claim 11, wherein the method further comprises displaying the transient basal delivery profile to a user.

19. The computer program of claim 11, wherein the transient basal delivery profile further comprises at least one additional basal profile to be delivered during at least one additional basal duration.

20. The computer program of claim 11, wherein the method further comprises administering the therapeutic fluid, and wherein such administration complies with pharmacokinetic and/or pharmacodynamic parameters of the therapeutic fluid.

21. A non-transitory computer readable medium comprising computer-executable instructions recorded thereon, which when executed by a processor of a therapeutic fluid dispensing device, causes the therapeutic fluid dispensing device to perform the method comprising:
  receiving, via an input, one or more transient basal related parameters;
  determining, via a basal programming application, a transient basal profile based on at least the one or more transient basal related parameters, wherein the transient basal profile comprises two or more phases and wherein at least one of the two or more phases includes either a basal overshot or a basal undershot.

22. The non-transitory computer readable medium of claim 21, wherein each of the two or more phases is characterized by a duration and at least one basal rate.

23. The non-transitory computer readable medium of claim 21, wherein receiving, via the input, of the one or more transient basal related parameters is from a remote control unit, a sensor, a glucometer or a continuous glucose monitor.

24. A therapeutic fluid dispensing device which dispenses a therapeutic fluid from a reservoir to a body of a patient, the therapeutic fluid dispensing device comprising:
  an input to receive one or more transient basal related parameters;
  a processor which has a basal programming application the operates thereon; and
  a pump which dispenses the therapeutic fluid from the reservoir to the body of the patient, wherein the basal programming application causes the processor to:
  receive, via the input, the one or more transient basal related parameters; and
  determine a transient basal profile which controls the therapeutic fluid delivered by the pump to the body of a patient during a period of transient change that is based on at least the one or more transient basal related parameters, wherein the transient basal profile comprises two or more phases and wherein at least one of the two or more-phases includes either a basal overshot or a basal undershot.

* * * * *